US006613379B2

United States Patent
Ward et al.

(10) Patent No.: US 6,613,379 B2
(45) Date of Patent: Sep. 2, 2003

(54) IMPLANTABLE ANALYTE SENSOR

(75) Inventors: W. Kenneth Ward, Portland, OR (US); Lawrence B. Jansen, Portland, OR (US); Ellen M. Anderson, Tualatin, OR (US)

(73) Assignee: iSense Corp., Portland, OR (US)

( * ) Notice: Subject to any disclaimer, the term of this patent is extended or adjusted under 35 U.S.C. 154(b) by 0 days.

(21) Appl. No.: 09/851,668

(22) Filed: May 8, 2001

(65) Prior Publication Data

US 2002/0169369 A1 Nov. 14, 2002

(51) Int. Cl.[7] .............................. B05D 3/00; G01N 27/26
(52) U.S. Cl. ................ 427/2.11; 427/2.24; 204/403.11; 204/415; 204/418
(58) Field of Search ............................... 427/2.11, 2.24, 427/58, 117, 118; 204/403.11, 415, 418; 422/68.1, 79; 436/63, 66

(56) References Cited

U.S. PATENT DOCUMENTS

| | | | |
|---|---|---|---|
| 3,890,049 A | 6/1975 | Collins et al. ............... 356/199 |
| 4,484,987 A | 11/1984 | Gough ........................ 204/1 T |
| 4,627,906 A | 12/1986 | Gough ........................ 204/415 |
| 4,650,547 A | 3/1987 | Gough ........................ 204/1 T |
| 4,655,880 A | 4/1987 | Liu ............................. 204/1 T |
| 4,832,797 A | 5/1989 | Vadgama et al. ........... 204/1 T |
| 4,938,860 A | 7/1990 | Wogoman .................... 204/403 |
| 5,030,310 A | 7/1991 | Wogoman .................... 156/252 |
| 5,165,407 A | 11/1992 | Wilson et al. ............... 128/635 |
| 5,200,051 A * | 4/1993 | Cozzette et al. ............ 204/403 |
| 5,286,364 A | 2/1994 | Yacynych et al. .......... 204/418 |
| 5,310,469 A | 5/1994 | Cunningham et al. ...... 204/403 |
| 5,401,376 A | 3/1995 | Foos et al. ................... 204/415 |
| 5,515,848 A | 5/1996 | Corbett, III et al. ........ 128/642 |
| 5,540,828 A | 7/1996 | Yacynych .................... 204/418 |
| 5,547,561 A * | 8/1996 | Vadgama et al. ............ 205/793 |
| 5,711,861 A | 1/1998 | Ward et al. .................. 204/403 |
| 5,766,934 A | 6/1998 | Guiseppi-Elie .......... 435/287.9 |
| 5,773,270 A * | 6/1998 | D'Orazio et al. ............ 435/177 |
| 5,914,026 A | 6/1999 | Blubaugh, Jr. et al. ..... 205/792 |
| 6,030,827 A | 2/2000 | Davis et al. ............. 435/287.1 |
| 6,060,327 A | 5/2000 | Keen ........................... 436/518 |
| 6,200,772 B1 * | 3/2001 | Vadgama et al. ............. 435/25 |

FOREIGN PATENT DOCUMENTS

EP    0575412 B1    8/1995

* cited by examiner

Primary Examiner—Brian K. Talbot
(74) Attorney, Agent, or Firm—Law Office of Timothy E. Siegel; Timothy E. Siegel

(57) ABSTRACT

An insertable analyte needle sensor, comprising a set of fine wires positioned together and a dielectric material covering a substantial portion of the fine wires but defining an opening filled with at least one partially permeable membrane. The wires may be treated with a gas plasma to facilitate membrane adherence. One membrane layer may comprise sulphonated polyethersulphone coated with silane.

6 Claims, 1 Drawing Sheet

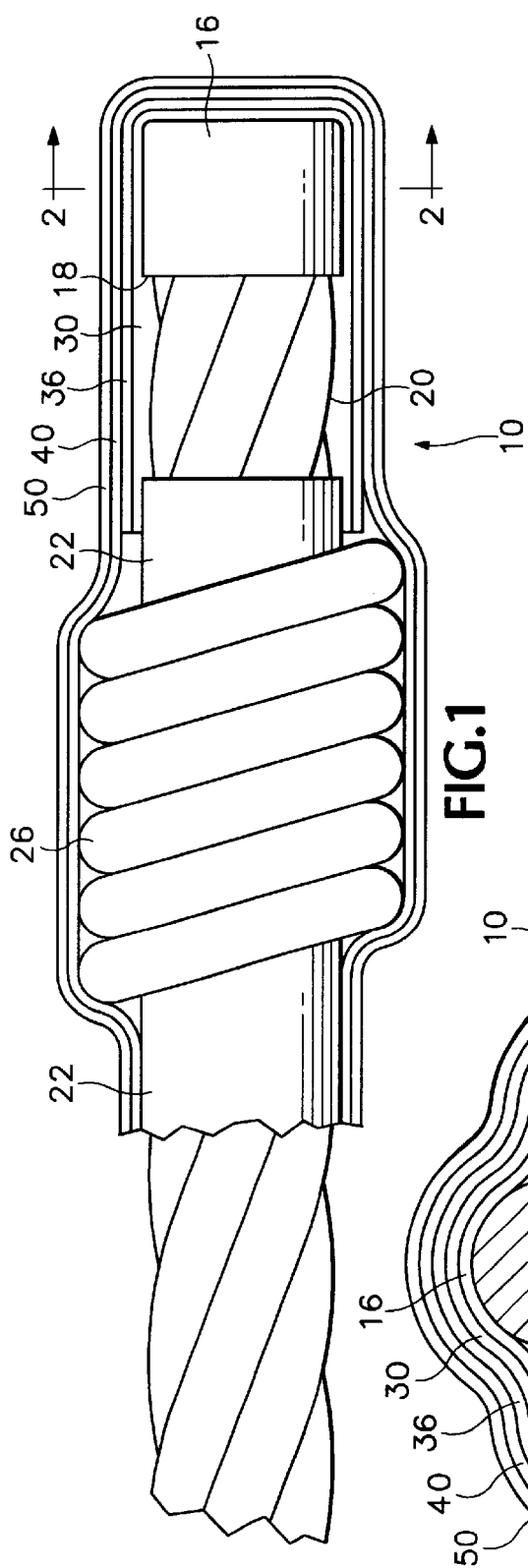
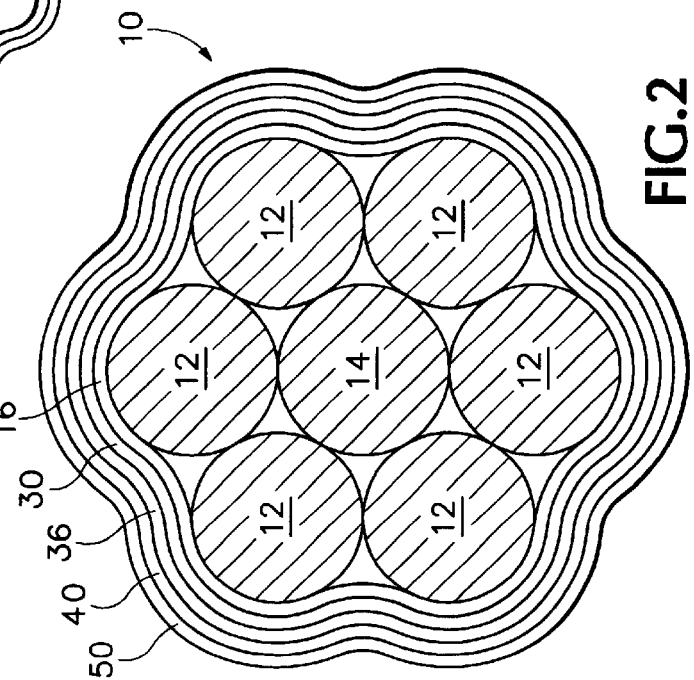

IMPLANTABLE ANALYTE SENSOR

BACKGROUND OF THE INVENTION

Blood glucose monitoring is a necessary tool for achieving glycemic control in diabetics. By permitting the patient to recognize when he is in a state of either hypo- or hyperglycemia, this monitoring enables the patient to appropriately intervene to maintain his health.

Hypoglycemia, the condition of having too little blood glucose, in severe form referred to as insulin shock, may lead to unconsciousness and death. As this may occur while the patient is asleep, monitoring methods that require action on the patient's part leave the patient vulnerable during his sleep. Frequent episodes of hyperglycemia lead to chronic diabetes complications, such as blindness, kidney failure and/or limb amputations.

Currently available methods of glucose monitoring require the patient to obtain a blood sample. Testing a blood specimen permits detection of both hypoglycemia and hyperglycemia. Unfortunately, the "finger stick" generally required for specimen collection is painful, so this type of testing is unpopular with patients and sometimes avoided. Newer, less painful methods are somewhat cumbersome.

Accordingly, continuous in vivo monitoring would yield great advantages by allowing prompter patient intervention. Many efforts to achieve this goal have been made over the years.

Generally, continuous in vivo monitoring is done with a sensor that produces an electrical current that is proportional to the blood or subcutaneous tissue glucose level. This is done by creating a reaction between immobilized glucose oxidase mixed with Bovine or Human Serum Albumin and glucose, to form gluconic acid and hydrogen peroxide. The hydrogen peroxide is oxidized at the platinum-indicating electrode 20 or anode surface, thereby freeing electrons that create a current and flow into the anode. Alternatively, or additionally, a current that is proportional to the dissolved oxygen level, which is decreased by the reaction in which glucose is oxidized, can be monitored. U.S. Pat. No. 5,165,407 ('407) and U.S. Pat. No. 5,711,861 ('861), which are both hereby incorporated by reference as if fully set forth herein, disclose in vivo devices for sensing glucose levels.

There are, however, a number of additional technical problems that must be addressed in the design of a glucose sensor. First, both dissolved oxygen and glucose are necessary to create the reaction that produces $H_2O_2$. Because dissolved oxygen is generally less abundant than glucose, the amount of $H_2O_2$ produced is primarily responsive to the concentration of dissolved oxygen, unless steps are taken to avoid this outcome. The region of linear response to glucose concentration may be increased by a membrane that restricts the passage of glucose molecules while permitting the relatively unrestricted passage of oxygen molecules. As a result, there is adequate dissolved oxygen to permit full registration of even relatively high concentrations of glucose. Permselective membranes currently in use have proven quite problematic, generally displaying poor performance.

One family of substances that has been suggested for use as a permeable selective (permselective) membrane are polyurethane/polyurea compositions containing silicone (taught, intra alia, in U.S. Pat. No. 5,882,494). Compounds from this family are discussed in some detail in U.S. Pat. No. 5,428,123, entitled COPOLYMER AND NON-POROUS SEMI-PERMEABLE MEMBRANE THEREOF AND ITS USE FOR PERMEATING MOLECULES OF PREDETERMINED MOLECULAR WEIGHT RANGE, which is hereby incorporated by reference as if fully set forth herein. As a term of art, the substances described and claimed in this patent are referred to as barrier breathing film (BBF). One characteristic of these substances is that they comprise a biocompatible, hydrophilic, segmented block polyurethane copolymer having a number average molecular weight of about 5,000 to 150,000, comprising about 5 to 45 wt % of at least one hard segment, and about 95 to 55 wt % of at least one soft segments comprising at least one hydrophilic, hydrophobic or amphipathic oligomer selected from the group consisting of aliphatic polyols, aliphatic and aromatic polyamines and mixtures thereof.

Another problem encountered is the presence in the interstitial fluid (ISF) of electroactive compounds other than $H_2O_2$. For example, the common pain reliever acetaminophen may be present in a patient's body and is capable of creating current flow into the anode. To prevent this interfering signal it has been suggested by Pankaj Vadgama et al. in U.S. Pat. No. 4,832,797, entitled ENZYME ELECTRODE AND MEMBRANE, to use a membrane of a sulphonated polyethersulphone (SPES) placed directly over the indicating electrode sensing surface. This layer generally prevents the passage of compounds larger than $H_2O_2$.

A review of the art reveals that it appears to have not yet been suggested to use a layer of BBF over a layer of SPES for both selectively passing oxygen and glucose and also filtering out interferents such as acetaminophen. This is not accidental as the general industry understanding has been that it is not possible to coat SPES with BBF due to the fact that the solvents available for creating a solution of BBF (typically dimethyl acetamide [DMAC] or related solvents) are the same ones that dissolve SPES. Accordingly, there has been a long felt need in the industry for a two membrane combination that can both selectively filter oxygen and glucose and can also filter out electro active interferents, despite the industry knowledge of both BBF and SPES. Moreover, it has been difficult to get the SPES to adhere strongly enough to the platinum-iridium surfaces so that a uniform coat of SPES is formed over the exposed platinum-iridium surface(s).

Another problem encountered in this type of sensor is the tendency for the sensitivity of the sensing surface to drift over time. One cause of this drift is growth of scar tissue about a sensor.

Another challenge for those designing needle sensors in general is that of potential breakage. It is unacceptable to leave a piece of a needle sensor within the human body. Accordingly, needle sensors that can be flexed many times (upwards of 1,000) are highly desirable compared with those that risk breakage with 30 or fewer flexures.

SUMMARY OF THE INVENTION

In a first separate aspect the present invention is an insertable analyte needle sensor, comprising a set of fine wires positioned together and a dielectric material covering a substantial portion of the fine wires but defining an opening filled with at least one partially permeable membrane.

In a second separate aspect the present invention is a method of producing an analyte sensor, comprising the steps of providing a conductive wire having an exposed surface and gas plasma treating the exposed surface of the conductive wire to remove oxidation. A SPES membrane is then applied over the platinum-iridium wire prior to the reformation of a layer of oxidation.

In a third separate aspect the present invention is a method of producing an analyte sensor in which, comprising the steps of providing a conductive wire having an exposed surface, applying a SPES membrane over the exposed surface of the conductive wire, and coating the SPES membrane with a solution of silane.

The foregoing and other objectives, features and advantages of the invention will be more readily understood upon consideration of the following detailed description of the preferred embodiment(s), taken in conjunction with the accompanying drawings.

BRIEF DESCRIPTION OF THE DRAWINGS

FIG. 1 is a greatly enlarged side cut-away view of a sensor according to the present invention.

FIG. 2 is a greatly enlarged cross-section view of the sensor of FIG. 1, taken along line 2—2 of FIG. 1.

DETAILED DESCRIPTION OF THE PREFERRED EMBODIMENT

A first preferred embodiment of a sensor 10 according to the present invention is in the form of an elongate structure, having a diameter of from 350 μm at its widest point, and 250 microns elsewhere, for easy insertion and acceptance into the subcutaneous tissue of a person or animal. The indicating electrode 20 is formed from a set of six platinum-iridium (90% Pt to 10% Ir) wires 12 twisted about a core wire 14. Core wire may be made of platinum-iridium for enhanced conductivity. In an alternative preferred embodiment, core wire 14 is made of steel for enhanced strength. Each wire 12 and 14, may be 58 μm in diameter, giving the set of wires a combined diameter of 174 μm. At the tip or distal end of the sensor is an ethylene tetrafluoroethylene (ETFE) hub 16 for facilitating sensor insertion and binding together the ends of the wires 12. Proximal from the distal tip is a laser-ablated cavity 18 through the ETFE to form the indicating electrode 20. Cavity 18 is preferably 2–10 mm in length. In one preferred embodiment cavity 18 circumscribes the sensor 10, although this is not necessary for sensor functioning. As it extends proximally from the cavity 18, the sensor 10 is coated with ETFE 22. The presence of ETFE coat 22 and hub 16 facilitate the retention of compounds in cavity 18.

Helically wrapped about the coating of ETFE 22 is a thin wire of Ag-AgCl, which serves as a cathode reference electrode 26. Immediately coating the fine wires in the laser ablated cavity is a membrane 30 of interferent-excluding sulphonated polyethersulphone (SPES). This prevents acetaminophen and other interferents from reaching the surface of the wires 12. Polyethersulphone is available from AMOCO Polymers, 4500 McGinnis Ferry Road, Alpharetta, Ga. 30202. The sulphonation process may be accomplished in accordance with the disclosure of Pankaj Vadgama et al. in U.S. Pat. No. 4,832,797, entitled ENZYME ELECTRODE AND MEMBRANE.

Constructing the sensor 10 presents a number of challenges that were discussed in the BACKGROUND section of this patent. First, there is the problem of getting the SPES to adhere to the underlying platinum-iridium wires with a strong enough bond so that there are no bare spots on the electrode, unprotected by SPES. Analysis has shown that the lack of good adherence found by earlier researchers was caused by a layer of oxidation that would form on the surface of the platinum-iridium wires. In one preferred embodiment of the present method this layer is removed by gas plasma treatment directly before the application of the SPES.

In greater detail, to gain proper adherence of the SPES to the platinum-iridium (Pt-Ir) surfaces, these surfaces are first washed with an acetone/ethanol application. In addition, these surfaces receive a radio frequency oxygen plasma etch at a vacuum of 0.8 Torr for 2 minutes at a frequency of 13.5 MHz. A Plasmod RF plasma chamber, available from March Instruments, Concord, Calif., 94520, may be used for this purpose.

In addition, to ensure complete coverage, a number of layers (typically between three and six) of SPES are added either through dip coating, loop coating or pipette coating to form layer 30.

In turn, covering membrane 30 is a membrane 36 of glucose oxidase ($GO_x$) mixed with bovine or human serum albumin (BSA) and glutaraldehyde. This is the chemically active layer that reacts with glucose and oxygen to form gluconic acid and hydrogen peroxide. The hydrogen peroxide provides electrons at the surface of the indicating electrode, which in this case is also the anode. Membrane 30 and its chemistry are already well known and are described in greater detail in U.S. Pat. No. 5,165,407, which has been incorporated by reference.

Covering membrane 36 is a permselective membrane 40 made of barrier breathing film (BBF), an amphiphobic polyurethane material noted in the BACKGROUND section of this patent application. As also noted in the background section, U.S. Pat. No. 5,882,494 (incorporated by reference) discloses the method of producing and the structure of BBF. In this instance, the BBF is produced to be about 2,000 times more permeable to oxygen than it is to glucose. In this manner sensor 10 responds to the glucose level, as even at a high glucose level there is adequate oxygen to combine with the available glucose. The BBF used is applied as an 8% w/w solution dissolved in DMAC, a low vapor pressure solvent. The BBF is not a hydrogel and has a water uptake of less than 2% at 24 hours.

Another problem encountered is the undesired removal of the SPES by the solvent in which the BBF is dissolved (typically DMAC). Although the layer of chemically active membrane coats the SPES at the point that the BBF is applied, this layer provides little protection for the SPES, although it is itself typically not completely removed by the application of the BBF. To prevent this removal the SPES is sulphonated by adding sulfuric acid to the SPES. This also lowers the pH of the resultant product.

For this reason, a layer of silane is added in order to stabilize the SPES layer and prevent its degradation by DMAC. For this purpose, N-2 amino ethyl, 3-aminopropyltrimethoxy silane (AATS) available from Aldrich chemical under designation #23, 577-6. The AATS solution was made as 20% AATS, 72% ethanol and 8% deionized water (all w/w). The AATS is applied between the next to the last and the last coats of SPES. The sensor is cured for 2 hours at 40 degrees C. after each coat of the SPES and oven-baked for 30 minutes at 150 degrees C. after the dip coat of AATS.

In some preferred embodiments there is a membrane 50, that is designed to encourage the growth of neovascularized tissue, covering permselective membrane 40. In other preferred embodiments membrane 50 is not present. In particular, if it is anticipated that a sensor will be replaced every few days, then membrane 50 is not needed because the sensor will be replaced before the neovascularized tissue can form.

To encourage the growth of neovascularized tissue a membrane should have finely spaced apertures with a typical diameter of about 5 μm. A number of materials are available for this function. Perhaps the most commonly available membrane for this purpose is expanded poly tetrafluoroethylene, available from W. L Gore and Associates, which has an Internet address of www.gore.com. U.S. patent application Ser. No. 09/441,642, filed Nov. 17, 1999 pending is assigned to the same assignee as this application and is hereby incorporated by reference as if fully set forth herein, describes a method for making an alternative sort of membrane for this purpose.

The terms and expressions which have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method of constructing a glucose sensor, comprising:
   (a) providing an electrode surface;
   (b) covering said electrode surface with a layer of with a layer of sulphonated polyether sulfone;
   (c) coating said layer of sulphonated polyether sulfone with a layer of silane; and
   (d) covering said layer of silane with a layer of oxygen/glucose permselective material, applied in an organic solvent.

2. The method of claim 1, in which said solvent is dimethyl acetamide.

3. The method of claim 1, in which the sensor is oven baked for over 15 minutes at a temperature of greater than 110° C.

4. The method of claim 1, further including applying an additional layer of sulphonated polyether sulfone, followed by an additional layer of silane.

5. The method of claim 1, in which said oxygen/glucose permselective material is a polyurethane based copolymer material.

6. The method of claim 1, in which a chemically active layer that reacts with glucose and oxygen is applied over said layer of silane, before application of said permselective layer, said organic solvent permeating through said chemically active layer to reach said silane, which prevents said organic solvent from substantially damaging said layer of sulphonated polyether sulfone.

* * * * *

UNITED STATES PATENT AND TRADEMARK OFFICE
CERTIFICATE OF CORRECTION

PATENT NO.   : 6,613,379 B2
DATED        : September 2, 2003
INVENTOR(S)  : Ward et al.

It is certified that error appears in the above-identified patent and that said Letters Patent is hereby corrected as shown below:

<u>Column 1,</u>
Line 2, after Descriptive Title, add heading and paragraph:

-- STATEMENT OF GOVERNMENT SUPPORT
    The invention which is the subject of this application was funded in part by CDC grant No.: RO CCR017796. The government retains certain rights in the invention. --

Signed and Sealed this

Thirteenth Day of April, 2004

JON W. DUDAS
*Acting Director of the United States Patent and Trademark Office*